United States Patent [19]

Bickford

[11] Patent Number: 4,879,997

[45] Date of Patent: Nov. 14, 1989

[54] ANESTHETIC VAPORIZER

[76] Inventor: Allan M. Bickford, 1581 Hubbard Rd., East Aurora, N.Y. 14052

[21] Appl. No.: 178,528

[22] Filed: Apr. 7, 1988

[51] Int. Cl.$^4$ ............................................. A61M 11/00
[52] U.S. Cl. ........................... 128/200.21; 128/203.12; 128/203.14; 128/203.26
[58] Field of Search ....................... 128/200.11, 200.14, 128/200.19, 200.21, 203.12, 203.14, 203.16, 203.17, 203.26, 204.13, 204.14, 204.17

[56] References Cited

U.S. PATENT DOCUMENTS

| | | | |
|---|---|---|---|
| 2,086,140 | 7/1937 | Silten | 128/203.14 |
| 2,553,446 | 5/1951 | Edmondson et al. | 128/203.14 |
| 3,158,154 | 11/1964 | Schreiber | 128/188 |
| 3,162,192 | 12/1964 | Gardner et al. | 128/203.14 |
| 3,192,924 | 7/1965 | Edmondson et al. | 128/188 |
| 3,313,298 | 4/1967 | Schreiber | 128/188 |
| 3,399,673 | 9/1968 | Jones et al. | 128/188 |
| 3,420,232 | 1/1969 | Bickford | 128/188 |
| 3,438,372 | 4/1969 | Sugg et al. | 128/203.14 |
| 3,530,905 | 9/1970 | Drager et al. | 141/18 |
| 3,534,732 | 10/1970 | Bickford | 128/188 |
| 3,565,133 | 2/1971 | Jones | 141/308 |
| 3,575,168 | 4/1971 | Jones | 128/188 |
| 3,578,042 | 5/1971 | Breiling | 141/301 |
| 3,630,438 | 12/1971 | Bickford | 236/93 |
| 3,651,805 | 3/1972 | Breiling | 128/188 |
| 3,671,024 | 6/1972 | Breiling | 128/203.14 |
| 3,714,391 | 1/1973 | Katzman et al. | 128/203.17 |
| 4,017,566 | 4/1977 | Seidel | 261/56 |
| 4,067,935 | 1/1978 | Jones et al. | 261/63 |
| 4,075,297 | 2/1978 | Seidel | 261/104 |
| 4,129,621 | 12/1978 | Jones et al. | 261/39 R |
| 4,477,395 | 10/1984 | Albarda | 261/131 |
| 4,484,576 | 11/1984 | Albarda | 128/202.22 |
| 4,587,966 | 5/1986 | Albarda | 128/202.22 |
| 4,611,590 | 9/1986 | Ryschka et al. | 128/203.14 |
| 4,693,853 | 9/1987 | Falb et al. | 261/39.1 |

Primary Examiner—Edgar S. Burr
Assistant Examiner—Kimberly L. Asher
Attorney, Agent, or Firm—Bean, Kauffman & Spencer

[57] ABSTRACT

An anesthetic vaporizer comprises a housing having a gas inlet and outlet, a vaporizing chamber, a vaporizing passage for passing carrier gas from the gas inlet to the vaporizing chamber and withdrawing gas enriched with vaporized anesthetic therefrom for passage towards the gas outlet via a flow control valve, a gas bypass passage for passing gas from the gas inlet via a bypass control valve for mixing with anesthetic enriched gas adjacent the gas outlet, wherein the bypass control valve is operated by a Teflon control rod in response to the temperature within the vaporizing chamber. The control rod is physically isolated relative to the vaporizing chamber, but disposed in intimate thermal contact therewith. The vaporizing passage includes an inlet portion in the form of a spiral tube having opposite ends connected to the gas inlet and the vaporizing chamber and an outlet portion defined by a spiral passage bounded by the exterior of the spiral tube and a pair of concentrically disposed wick sleeves disposed in surface engagement with the spiral tube and in fluid communication with the vaporizing chamber; wherein one end of the spiral passage communicates with the vaporizing chamber and an opposite end communicates with the flow control valve.

7 Claims, 3 Drawing Sheets

ANESTHETIC VAPORIZER

BACKGROUND OF THE INVENTION

The invention relates generally to anesthetic vaporizers of the type in which a gas stream directed through the vaporizer is divided into two streams, namely, a first or carrier gas stream passed through a vaporizing chamber containing a volatile liquid anesthetic and a second or bypass stream to be combined with the first stream after it has become saturated with anesthetic for subsequent discharge from the vaporizer. The streams of gas are controlled by flow control valves, wherein one of such valves is automatically adjustable in response to the temperature of the first stream after it become saturated with anesthetic or the temperature existing within the vaporizing chamber.

In my prior U.S. Pat. Nos. 3,534,732 and 3,630,438, the flow control valve for the first or carrier gas stream is a composite control valve, wherein one valve part is formed of metal and a cooperating valve part is formed of plastic material having a relatively large positive linear coefficient of thermal expansion, that is, the material expands upon an increase in temperature, within the normal temperature range in which a vaporizer is normally used. The plastic material employed was preferably a fluorocarbon of which polytetrafluoroethylene, known as PTFE or TFE or more generally by the trademark Teflon, is an example. A significant problem with this material encountered in actual practice was its tendency to swell when exposed to various anesthetic materials with the result that stability problems were encountered in the calibration of the flow control valve in which it was employed This problem was minimized to some extent by presaturating the material with the anesthetic, under pressure, but calibration drift over time was experienced, due to variations in the saturation process or drying out of the material "on the shelf" prior to its being placed in service.

SUMMARY OF THE INVENTION

The present invention is directed towards improvements in anesthetic vaporizers.

In accordance with the present invention, problems encountered with vaporizers of the general type described with reference to U.S. Pat. Nos. 3,534,732 and 3,630,438 are overcome by physically isolating a Teflon temperature responsive valve control member from anesthetic passing through a vaporizer, while providing for intimate thermal contact thereof with anesthetic gas present in the vaporizing chamber. More specifically, the present invention contemplates fluid sealing a Teflon rod within a metal casing having a closed end arranged to extend into the vaporizing chamber and a fluid sealed opposite end, which is operatively associated with an element of a bypass control valve and displaceable axially of the metal casing in response to axial extensions/contractions of the Teflon rod for purposes of controlling flow of bypass gas prior to its being combined with carrier gas passing from the vaporizing chamber.

The present vaporizer additionally features an improved arrangement for controlling flow of carrier gas from the vaporizing chamber so as to insure that same is at all times fully saturated with anesthetic. Specifically, it is contemplated that carrier gas will be passed to the vaporizing chamber through a spirally wound solid walled tube, which is sandwiched between a pair of cylindrically shaped wick members arranged to immerse their lower ends in liquid anesthetic. The tube cooperates with the wick members to define a spiral discharge passageway for the carrier gas, which has its lower and upper ends disposed in flow communication with the vaporizing chamber at a point above the level of the liquid anesthetic and its upper end disposed in flow communication with the flow control valve for the carrier gas.

BRIEF DESCRIPTION OF THE DRAWINGS

The nature and mode of operation of the present invention will now be more fully described in the following detailed description taken with the accompanying drawings wherein.

DETAILED DESCRIPTION

An anesthetic vaporizer formed in accordance with the present invention is designated as 10 and shown as generally including a cup-shaped container 12 and a head assembly 14, which is maintained in seated engagement with the open upper end of container 12 by a stepped diameter mounting bolt device 16.

Figure 1:
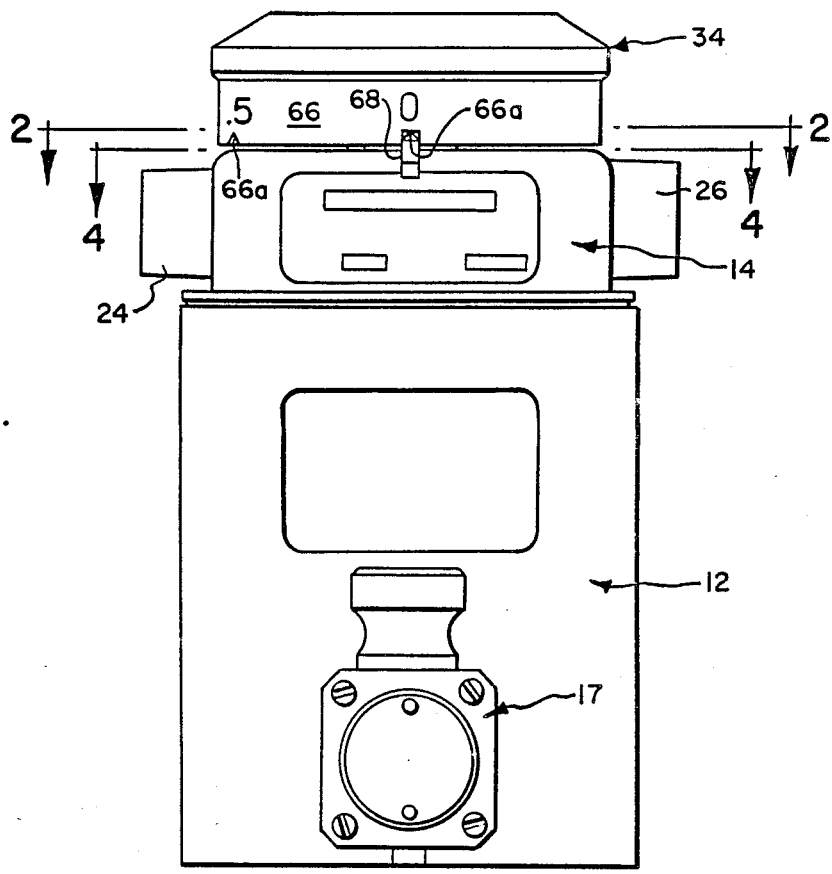
FIG. 1 is a front elevational view of an anesthetic vaporizer embodying the present invention.
Figure 2:
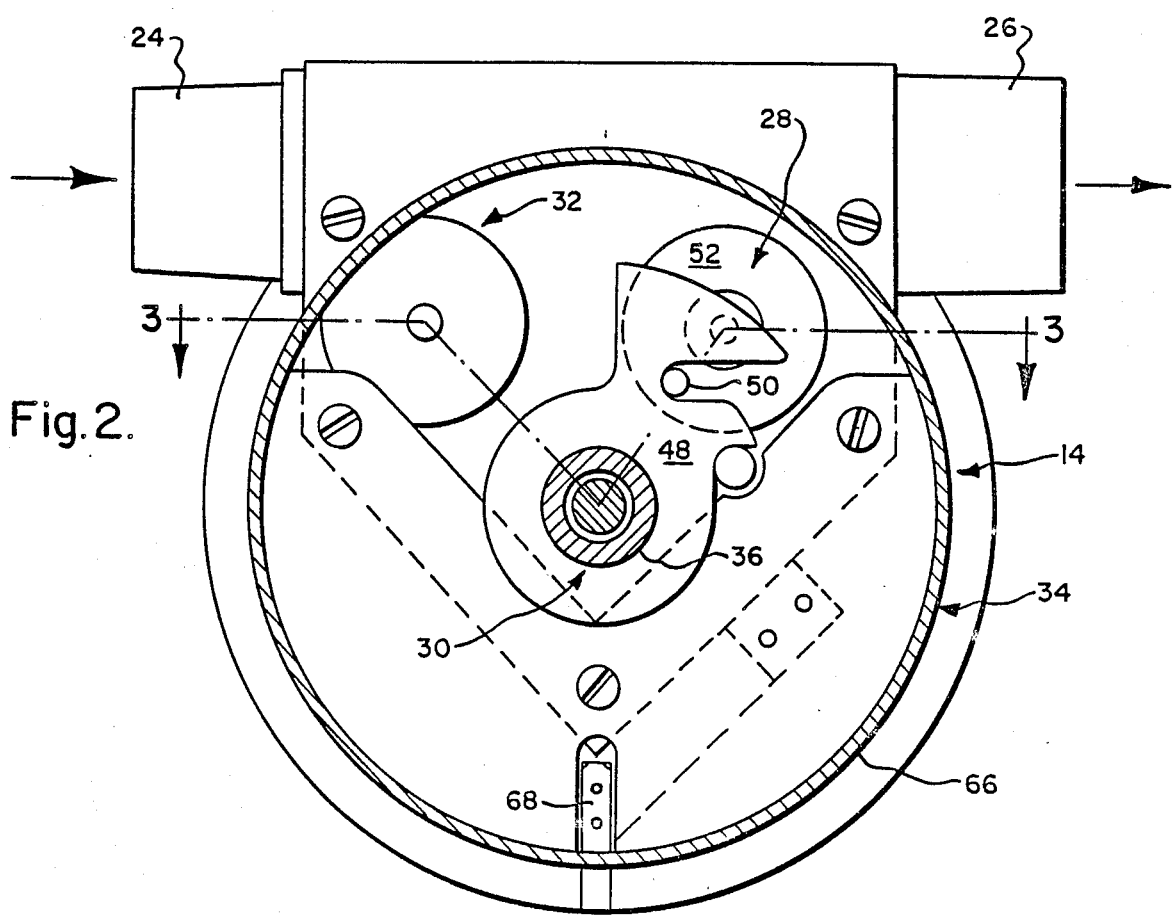
FIG. 2 is a sectional view taken generally along line 2—2 in FIG. 1.

Container 12 is fitted adjacent its lower end with funnel/drain assembly 17, shown only in FIG. 1, through which a desired charge of liquid anesthetic 18 may be supplied to or drained from the lower portion of a vaporizing chamber 20, which is generally bounded by the lower end of the container and a fluid sealed space occupying device or can 22 clamped concentrically within the container against head assembly 14 by bolt device 16.

Head assembly 14 is fitted with gas inlet and outlet fittings 24 and 26, respectively; an ON/OFF valve 28; a flow control valve 30; a bypass control valve 32; a rotatably supported cover or knob 34 for controlling operation or adjustment of valves 28 and 30; and fluid passageway system to be subsequently described primarily with reference to FIGS. 4, 5, 6A and 6B for affording flow communication between the inlet and outlet fittings and the vaporizing chamber under control of the valves.

Figure 3:
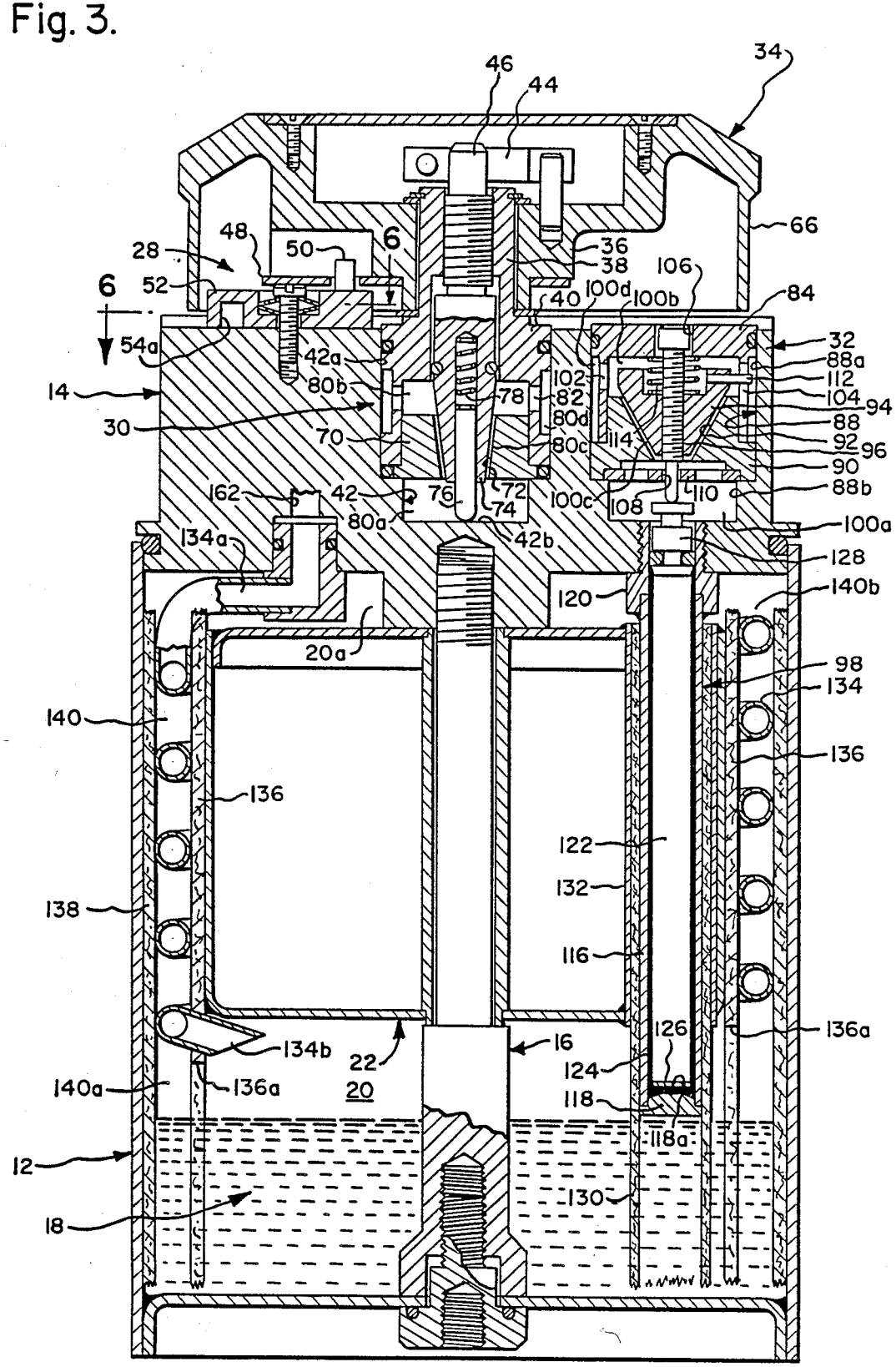
FIG. 3, is a sectional view taken generally along line 3—3 in FIG. 2.

Cover 34 is best shown in FIG. 3 as being formed with a hub 36 journalled on a sleeve portion 38, which defines an upper end of a mixing control valve housing part 40 non-movably fixed within an upper end portion 42a of a stepped diameter bore 42 formed in head assembly 14, and as being coupled by a clamp device 44 for rotation with a mixing control valve adjustment screw 46. Hub 36 additionally carries a cam plate 48 shaped and arranged to engage with a pin 50 for purposes of effecting rotation of a rotatably supported, circular valve plate 52 comprising the movable part of ON/OFF valve 28 between valve on or open and off or closed positions shown respectively in FIGS. 6A and 6B. As will be understood by viewing FIGS. 3, 6A and 6B, valve plate or disc 52 is provided with a pair of downwardly opening arcuate slots 54a and 54b for purposes of selectively providing flow communication between the upper ends of vertically extending annularly spaced, fluid passages 56, 58 and 60 and between the upper ends of vertically extending annularly spaced fluid passageways 62 and 64, respectively.

Cover 34 is additionally formed with an outer cylindrical rim part 66 whose depending annular edge is provided with a plurality of annularly spaced notches or recesses 66a sized to removably receive a spring biased latch or detent device 68 fixed to head assembly 14 beneath the cover 34 for purposes of releasably retaining the cover in manually selected, rotatably adjusted positions thereof.

Flow control valve 30 is shown in FIG. 3 as additionally including a second housing part 70, which is fixed within the lower end of housing part 40 and serves to define a conical valve seat 72; and a frusto-conical valve element 74, which depends from adjustment screw 46 concentrically within valve seat 72 and carries a pin 76 biased by a spring 78 for engagement with the bottom end of a reduced diameter lower end portion 42b of bore 42. Housing part 70 cooperates with lower end portion 42b of bore 42 and housing part 40 to define, respectively, lower and upper valve chambers 80a and 80b disposed in flow communication with a conically shaped, annular passage 80c defined by facing surfaces of valve seat 72 and valve element 74. Upper housing part 40 cooperates with upper end portion 42a of bore 42 to define an annular chamber 80d, which is disposed in flow communication with upper valve chamber 80b by ports 82 extending radially through housing part 40.

Bypass control valve 32 is shown in FIG. 3 as including an upper housing part 84 which is fitted within an upper end portion 88a of a stepped diameter bore 88 formed in head assembly 14; a lower or second housing part 90 which is fitted within both upper housing part 84 and end portion 88a and serves to define a conical valve seat 92; a frusto-conical valve element 94, which is adjustably supported by an adjustment screw 96; and a temperature responsive device 98 adapted to control positioning of valve element 94 relative to valve seat 92. Lower housing part 90 cooperates with a lower end portion 88b of bore 88 and upper housing part 84 to define, respectively, lower and upper valve chambers 100a and 100b disposed in flow communication with a conically shaped annular passage 100c defined by facing surfaces of valve seat 92 and valve element 94. Upper housing part 90 cooperates with upper end portion 88a of bore 88 to define an annular chamber 100d, which is disposed in flow communication with upper valve chamber 100b by ports 102 and an axially extending guide slot 104 opening radially of the upper housing part.

Adjustment screw 96 threadably engages with valve element 94 and has its upper end disposed to rotatably/slidably engage within a through bore 106 formed centrally of upper housing part 84. The lower end of screw 96 is rotatably/slidably supported within a through bore 108, which is formed centrally of an apertured guide plate 110 positionally located by lower housing part 90, and is arranged to abut against the upper end of temperature responsive device 98. Valve element 94 is constrained against rotation relative to valve seat 92 via a guide pin 112 slidably received within guide slot 104 and is biased in a direction relatively away from upper housing part 84 and towards valve seat 92 by a coil type compression spring 114.

Temperature responsive device 98 is shown in FIG. 3 as comprising a thermally conductive tubular metal housing 116, which has its lower end fluid sealed by an end cap 118 having a dome-shaped inner or upper end or bearing surface 118a and its upper end fluid sealed and supported to depend from head assembly 14 by a threaded mounting fitting 120. A cylindrically shaped rod 122 is located concentrically within housing 116 and placed in uniform thermal contact therewith by means of an enveloping layer of a suitable heat conducting gel-like material 124 formed of powered metal suspended in a carrier, as for instance powered aluminum in a silicone grease. Rod 122 is formed from a plastic material having a relatively large positive linear coefficient of thermal expansion within the normal temperature range in which vaporizer 10 is normally used, e.g. room temperature, and is preferably polytetrafluoroethylene and known commercially as TFE or under the trademark Teflon. The lower and upper ends of rod 122 abut against a metal disc 126 and a slide member 128 with disc 126 being arranged to engage with end cap surface 118a and with slide member 128 being arranged to extend upwardly in a fluid sealed relation within mounting fitting 120 for underengagement with the lower free end of adjustment screw 96. The diameter and length of rod 122 are chosen to insure that the rod will not bend under all loading conditions it is expected to encounter during use. Housing 116 is surrounded by a sleeve of closely fitting wicking material 130, which has its lower end immersed within anesthetic 18 and its upper end fitted within a mounting tube 132 fixed to extend vertically through space occupying device 22. With this arrangement, Teflon rod 122 is exposed or subjected to the temperature existing within vaporizing chamber 20 without being exposed to the anesthetic contained therein.

Again referring to FIG. 3, it will be noted that the annular space between the cylindrical inner wall of container 12 and the cylindrical outer wall of device 22 is occupied by a spirally wound tube 134 having inlet and outlet ends 134a and 134b; and inner and outer sleeves of wicking material 136 and 138. Sleeves 136 and 138 have their lower ends immersed within anesthetic 18 and their upper ends arranged in surface engagement with device 22 and container 12, respectively, and to cooperatively engage with tube 134 to define a spiral passage or flow path 140 having an inlet end 140a disposed in flow communication with chamber 20 immediately above anesthetic 18 by forming inner sleeve 136 with flow passages in the form of slots 136a and an outlet end 104b disposed in flow communication with an upper annular chamber 20a, which is arranged vertically between device 22 and head assembly 14.

Figure 4:
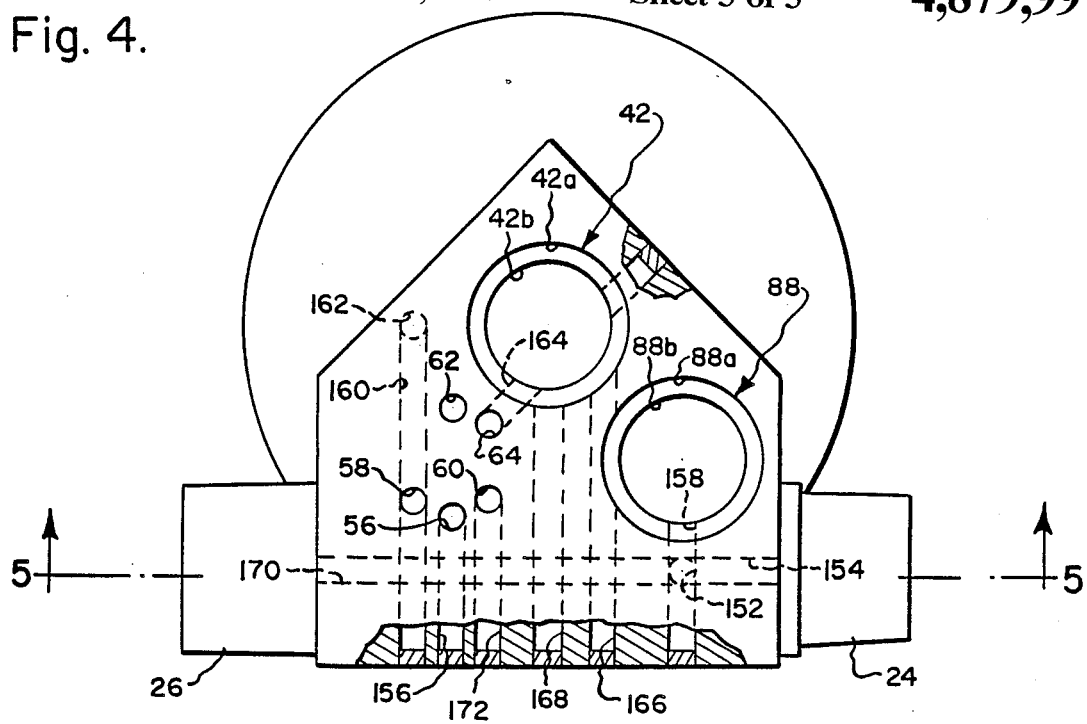
FIG. 4 is a sectional view taken generally along line 4—4 in FIG. 1.
Figure 5:
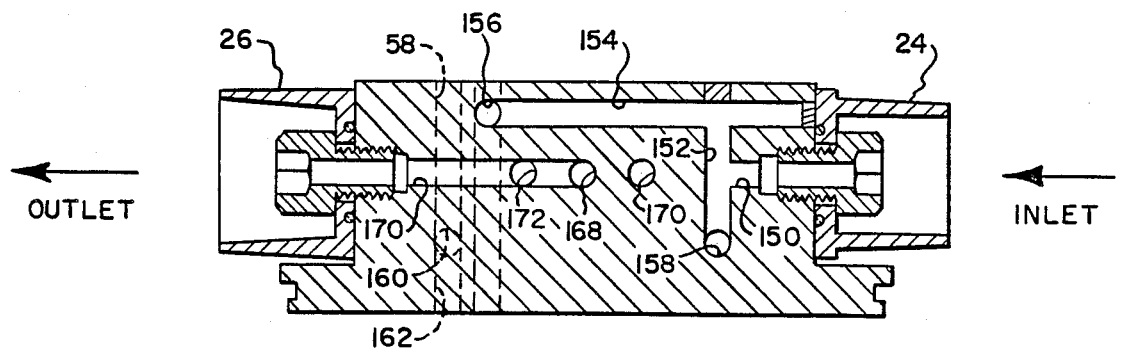
FIG. 5 is a sectional view taken generally along line 5—5 in FIG. 4.

Referring now particularly to FIGS. 4 and 5, it will be understood that inlet 24 is disposed in flow communication with ON/OFF valve 28 via interconnected passageways 150, 152, 154, 156 and passage 56; and in flow communication with lower chamber 100a of bypass control valve 32 via passageways 150, 152 and 158. Gas introduced into lower chamber 100a is permitted to exit therefrom under the control of valve element 94 through passage 100c into upper chamber 100b from which it is free to pass outwardly through ports 102 and slot 104 into annular chamber 100d.

Figure 6A:
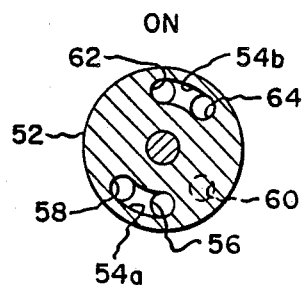
FIGS. 6A and 6B are fragmentary sectional views taken along line 6—6 in FIG. 3 and illustrating the ON and OFF positions of the shutoff valve.

When ON/OFF valve 28 is in its ON position shown in FIG. 6A, gas exiting from passage 56 is channeled by slot 54a to pass into the upper end of passage 58 for flow to inlet end 134a of spiral tube 134 via interconnecting passages 160 and 162. Gas passing through spiral tube 134 is discharged through tube outlet end 134b into vaporizing chamber 20 where it picks up anesthetic vapor. Partially saturated gas present at the top of chamber 20 is permitted to escape via inlet 140a for movement upwardly along spiral path 140 for discharge as fully saturated gas via outlet 140 into upper chamber 20a. Upper chamber 20a is in turn disposed in flow communication with ON/OFF valve 28 via passage 62. With ON/OFF valve 28 in its open position, saturated gas exiting from passage 62 is channeled by slot 54b to pass into the upper end of passage 64 for flow via interconnected passage 164 to lower chamber 80a of flow control valve 30. Saturated gas introduced into lower chamber 80a is permitted to exit therefrom under the control of valve element 74 through passage 80c into upper chamber 80b from which it is free to pass outwardly through ports 82 into annular chamber 80d. It will be understood that annular chamber 80d is disposed in flow communication with annular chamber 100d of bypass control valve 32 by a passage 166, such that gas supplied to bypass control valve 32 directly from inlet 24 is permitted to mix with saturated gas within annular chamber 80d prior to discharge from the vaporizer through outlet 26 via interconnected passageways 168 and 170.

Figure 6B:
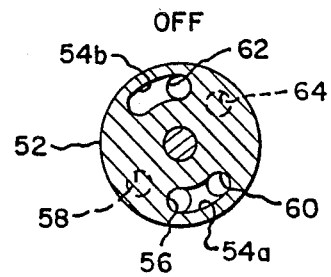

When ON/OFF valve 28 is in its OFF position shown in FIG. 6B, gas from inlet 24 exiting from passage 56 is channeled by slot 54a to pass into the upper end of passage 60, which connects directly with vaporizer outlet 26 via interconnected passageways 172 and 170. Gas from inlet 24 may continue to be passed to vaporizer outlet 26 via bypass control valve 32, annular chamber 80d of mixing control valve 30 and passages 168 and 170. However, the escape of saturated gas from vaporizing chamber 20 and/or the mixing thereof with gas supplied directly from inlet 24 is prevented, due to the closing of passages 58 and 64 by ON/OFF valve 28 while in OFF condition.

The use of Teflon rod 122, which has a substantial dimensional change with temperature variation within the operating range of vaporizer 10, allows for significant movement for valve actuation purposes, as compared to a metal temperature responsive member, and with sufficient force to provide positive positioning of the valve element 94. This relatively large permissive range of movement makes possible a wider tolerance for any amount of change in the shape/size of valve flow passage 100c, which might tend to occur due to jarring of the vaporizer. The mode of mounting Teflon rod 122 serves to completely isolate it from fluid contact with the anesthetic, so as to prevent calibration problems heretofore encountered as a result of swelling of the Teflon material, while at the same time place the rod in intimate thermal contact with the anesthetic in order to provide prompt response to variation in temperature conditions existing within vaporizing chamber 20.

In the design of bypass valve 32, the sensitivity of the valve in response to temperature-caused movements of the Teflon rod 122 can be tailored to the application of vaporizer 10 or the type of anesthetic used by selecting the included angle of valve element 94, which can be very small or up to 180°. The starting or initial valve gap or the thickness of passage 100c can be adjusted externally by applying turning movement to the upper end of screw 96.

What is claimed is:

1. An anesthetic vaporizer including in combination:
   a container for receiving liquid volatilizable anesthetic;
   a head assembly supported on said container, said assembly having an inlet for receiving a gas and an outlet for discharging a mixture of the gas and volatilized anesthetic;
   first conduit means for conducting said gas from said inlet to said container so as to entrain vaporized anesthetic therein and create a preliminary mixture of said gas and volatilized anesthetic and conducting said preliminary mixture from said container towards said outlet, and including an adjustable control valve disposed in said assembly for regulating the flow of said preliminary mixture;
   second conduit means for conducting said gas from said inlet for mixing with said preliminary mixture within said assembly at a point intermediate said flow control valve and said outlet to create said mixture, and including an adjustable bypass control valve disposed in said assembly for regulating the flow of said gas prior to mixing thereof with said preliminary mixture
   said bypass control valve has first and second members adjustable one relative to the other to control fluid flow of said gas therebetween; and
   temperature responsive means extending from within said container into said assembly for connection to one of said members and including a plastic material subject to swelling upon exposure to said anesthetic, said plastic material having a positive linear coefficient of thermal expansion which is greater than the coefficient of thermal expansion of the other of said members for automatically adjusting said fluid flow of said gas between said members in response to temperature changes, thermally conductive means for receiving said plastic material and being disposed within said container and having an open end opening into said assembly in alignment with said one of said members, said conductive means placing said plastic material in direct thermal communication with said preliminary mixture within said container while physically isolating said plastic material from physical contact with said preliminary mixture, and means extending through said open end for connecting said plastic material to said one of said members.

2. An anesthetic vaporizer according to claim 1, wherein said container has a cylindrical side wall and top and bottom walls and is fitted with a space occupying device cooperating with said container to define a lower chamber for receiving said liquid volatilizable anesthetic an upper chamber and an annular passage adjacent said cylindrical side wall extending between said lower and upper chambers; and
   said first conduit means includes a spirally wound tube having a fluid impermeable wall with one end thereof disposed in flow communication with said inlet and a second end thereof disposed in flow communication with said lower chamber above the level of said liquid volatilizable anesthetic, and a spiral passage bounded by the coils of said tube and a pair of cylindrical wick members extending one between said tube and said cylindrical side wall and the other between said tube and said space occupying device, said pair of wick devices having lower ends thereof extending into said lower chamber for immersion within said liquid volatilizable anesthetic, said spiral passage having one end disposed in flow communication with said lower chamber above the level of said liquid volatilizable anesthetic and a second end disposed in flow communication with said upper chamber, and said upper chamber is disposed in flow communication with said flow control valve.

3. An anesthetic vaporizer including in combination:
a container for receiving liquid volatilizable anesthetic;
an inlet for receiving a gas and an outlet for discharging a mixture of the gas and volatilized anesthetic;
first conduit means for conducting said gas from said inlet to said container so as to entrain vaporized anesthetic therein and create a preliminary mixture of said gas and volatilized anesthetic and conducting said preliminary mixture towards said outlet, and including an adjustable control valve for regulating the flow of said preliminary mixture;
second conduit means for conducting said gas from said inlet for mixing with said preliminary mixture at a point intermediate said flow control valve and said outlet to create said mixture, and including an adjustable bypass control valve for regulating the flow of said gas prior to mixing thereof with said preliminary mixture; and
one of said valves has first and second members adjustable one relative to the other to control fluid flow therebetween and temperature responsive means connected to one of said members and including a plastic material subject to swelling upon exposure to various anesthetic materials, said plastic material having a positive linear coefficient of thermal expansion which is greater than the coefficient of thermal expansion of the other of said members for automatically adjusting said fluid flow between said members in response to temperature changes, and said plastic material is disposed in direct thermal communication with said preliminary mixture, while being isolated from physical contact therewith, said other of said members is positionally fixed, and said one of said valves includes spring means for resiliently biasing said one of said members relatively towards said other of said members, and said plastic material is coupled to said one of said members for moving same away from said other of said members upon temperature induced expansion of said plastic material by means for adjusting the position of said one of said members relative to said plastic material and said means for adjusting the position of said one of said members guides said one of said members for movement relative to said other of said members.

4. An anesthetic vaporizer according to claim 3, wherein said first and second members are included in said bypass control valve.

5. An anesthetic vaporizer including in combination:
a container for receiving liquid volatilizable anesthetic;
an inlet for receiving a gas and an outlet for discharging a mixture of the gas and volatilized anesthetic;
first conduit means for conducting said gas from said inlet to said container so as to entrain vaporized anesthetic therein and create a preliminary mixture of said gas and volatilized anesthetic and conducting said preliminary mixture towards said outlet, and including an adjustable control valve for regulating the flow of said preliminary mixture;
second conduit means for conducting said gas from said inlet for mixing with said preliminary mixture at a point intermediate said flow control valve and said outlet to create said mixture, and including an adjustable bypass control valve for regulating the flow of said gas prior to mixing thereof with said preliminary mixture; and
one of said valves has first and second members adjustable one relative to the other to control fluid flow therebetween and temperature responsive means connected to one of said members for automatically adjusting said fluid flow between said members in response to temperature changes, and said temperature responsive means is disposed in direct thermal communication with said preliminary mixture, while being isolated from physical contact therewith, said other of said members is positionally fixed, said one of said members is resiliently biased relatively towards said other of said members, said temperature responsive means is a plastic material in the form of an elongated rod having a positive linear coefficient of thermal expansion which is greater than that of said other of said members, and there is further provided a thermally conductive tube means sized to receive said rod and having an open end non-movably fixed relative to said other of said members in axial alignment with said one of said members and a closed end disposed within said container, a thermally conductive filler filling the space between said tube means and said rod, an end closure seal movably carried within said open end of said tube means and having axially opposite ends thereof disposed in bearing engagement with one end of said rod and said one of said members, said rod having an opposite end bearing on said closed end, and a wick having one end enclosing said tube means and an opposite end disposed for receipt within said liquid volatilizable anesthetic, said end closure seal coupling said rod to said one of said members for moving said one of said members away from said other of said members upon temperature induced expansion of said rod.

6. An anesthetic vaporizer including in combination:
a container for receiving liquid volatilizable anesthetic, said container having a cylindrical side wall and top and bottom walls and is fitted with a space occupying device cooperating with said container to define a lower chamber for receiving said liquid volatilizable anesthetic, an upper chamber and an annular passage adjacent said cylindrical side wall extending between said lower and upper chambers;
an inlet for receiving a gas and an outlet for discharging a mixture of the gas and volatilized anesthetic;
first conduit means for conducting said gas from said inlet to said container so as to entrain vaporized anesthetic therein and create a preliminary mixture of said gas and volatilized anesthetic and conducting said preliminary mixture towards said outlet, and including a spirally wound tube having a fluid impermeable wall with one end thereof disposed in flow communication with said inlet and a second end thereof disposed in flow communication with said lower chamber above the level of said liquid volatilizable anesthetic, a spiral passage bounded by the coils of said tube and a pair of cylindrical wick members extending one between said tube and said cylindrical side wall and the other between said tube and said space occupying device, said pair of wick devices having lower ends thereof extending into said lower chamber for immersion within said liquid volatilizable anesthetic, said spiral passage having one end disposed in flow communication with said lower chamber above the level of said liquid volatilizable anesthetic and a second end disposed in flow communication with said upper chamber, and an adjustable flow control valve for regulating the flow of said preliminary mixture from said upper chamber to said outlet;

second conduit means for conducting said gas from said inlet for mixing with said preliminary mixture at a point intermediate said flow control valve and said outlet to create said mixture, and including an adjustable bypass control valve for regulating the flow of said gas prior to mixing thereof with said preliminary mixture; and one of said valves is adjustable in response to the temperature existing within said lower chamber.

7. An anesthetic vaporizer including in combination:

a container for receiving liquid volatilizable anesthetic;

an inlet for receiving a gas and an outlet for discharging a mixture of the gas and volatilized anesthetic;

first conduit means for conducting said gas from said inlet to said container so as to entrain vaporized anesthetic therein and create a preliminary mixture of said gas and volatilized anesthetic and conducting said preliminary mixture towards said outlet, and including an adjustable control valve for regulating the flow of said preliminary mixture;

second conduit means for conducting said gas from said inlet for mixing with said preliminary mixture at a point intermediate said flow control valve and said outlet to create said mixture, and including an adjustable bypass control valve for regulating the flow of said gas prior to mixing thereof with said preliminary mixture; and one of said valves has first and second members adjustable one relative to the other to control fluid flow therebetween and temperature responsive means connected to one of said members and including a plastic material subject to swelling upon exposure to various anesthetic materials, said plastic material having a positive linear coefficient of thermal expansion which is greater than the coefficient of thermal expansion of the other of said members for automatically adjusting said fluid flow between said members in response to temperature changes, and said plastic material is disposed in direct thermal communication with said preliminary mixture, while being isolated from physical contact therewith, said other of said members is positionally fixed, and said one of said valves includes spring means for resiliently biasing said one of said members relatively towards said other of said members, and said plastic material is coupled to said one of said members for moving same away from said other of said members upon temperature induced expansion of said plastic material by means for adjusting the position of said one of said members relative to said plastic material, said plastic material is in the form of an elongated rod, and there is further provided a thermally conductive tube means sized to receive said rod and having an open and non-movably fixed relative to said other of said members in axial alignment with said one of said members and a closed end disposed within said container, a thermally conductive filler filling the space between said tube means and said rod, an end closure seal movably carried within said open end of said tube means and having axially opposite ends thereof disposed in bearing engagement with one end of said rod and said means for adjusting the position of said one of said members, said rod having an opposite end bearing on said closed end, and a wick having one end enclosing said tube means and an opposite end disposed for receipt within said liquid volatilizable anesthetic.

* * * * *